United States Patent [19]
Rosbrook et al.

[11] Patent Number: 5,924,421
[45] Date of Patent: Jul. 20, 1999

[54] SKIN PROTECTION DEVICE AND METHOD OF USING SAME

[76] Inventors: Marlo Rosbrook, 13593 Tradition St., San Diego, Calif. 92128; Wendy Jo Reitmeyer, 820 Beryl St., San Diego, Calif. 92109

[21] Appl. No.: 09/020,915

[22] Filed: Feb. 9, 1998

[51] Int. Cl.[6] .................................................. A61M 16/00
[52] U.S. Cl. ............................. 128/207.14; 128/207.17; 604/174
[58] Field of Search ......................... 128/207.14, 207.17, 128/200.26, 207.29; 604/174–179

[56] References Cited

U.S. PATENT DOCUMENTS

| | | | |
|---|---|---|---|
| 4,313,437 | 2/1982 | Martin | 128/207.17 |
| 5,271,745 | 12/1993 | Fentress et al. | |
| 5,282,463 | 2/1994 | Hammersley | 128/207.15 |
| 5,368,023 | 11/1994 | Wolf | |
| 5,551,421 | 9/1996 | Noureldin et al. | |
| 5,749,360 | 5/1998 | Lacey et al. | 128/207.14 |
| 5,819,734 | 10/1998 | Deily et al. | 128/207.17 |

*Primary Examiner*—John G. Weiss
*Assistant Examiner*—Charles Anderson
*Attorney, Agent, or Firm*—Jerry R. Potts

[57] ABSTRACT

A new and improved skin protection device helps maintain the fluid and mechanical interconnection between a tracheostomy tube and an associated ventilator tube coupler while simultaneously substantially spacing the skin engaging surface of the tracheostomy tube external housing from the neck skin of a patient user. The device includes a fabric covered U-shaped elastic cradle member that has an attachment arrangement to removably attach the device to the tracheostomy tube and space it from the skin of the patient A removably attachable cradle cover is provided for attachment to the cradle member between its spaced apart tracheostomy attachment arms so as to cover the mechanical interconnection between the tracheostomy tube housing and the ventilator tube coupler to help prevent the under chin neck skin of the patient from becoming pinched in the mechanically interconnection between the tracheostomy tube and the ventilator tube coupler. The method of use the device includes attaching the cradle member to the tracheostomy tube, pulling it into tension by extending its length to pass over an end portion of the ventilator tube coupler and releasing the cradle member to engage in tension the ventilator tube coupler.

13 Claims, 8 Drawing Sheets

SKIN PROTECTION DEVICE AND METHOD OF USING SAME

TECHNICAL FIELD

The present invention relates in general to respiratory devices and the method of using them. More particularly, the present invention relates to a skin protection device and a method of using the protection device to help maintain the fluid and mechanical interconnection between a tracheostomy tube and ventilator tube for patient assisted breathing while simultaneously helping to protect the neck skin of the patient from making intimate direct contact with the skin engaging external surfaces of the tracheostomy tube.

BACKGROUND ART

Ventilators are used for patient assisted breathing when a person is unable to breathe on his or her own volition. In order to facilitate interconnecting such a ventilator with a surgically implanted tracheostomy tube, various tubing and couplers are utilized. While such a breathing system facilitates patient assisted breathing, there are several problems associated with keeping the ventilator tubing properly attached to the tracheostomy tube. In this regard, often times, the ventilator tubing will "pop off" unexpectedly from the tracheostomy tube. For example, if there is resistance with the air supply being delivered, or if the patient takes a larger than usual breath, the ventilator tubing may become detached from the tracheostomy tube.

Other times the ventilator tubing may become dislodged. In this regard, because of bodily fluid secretions that build up and coat the interior of the tubing allowing it to easily slide, the tubing may become accidentally dislodged. Moreover, if a patient suddenly and unexpectedly begins to cough the rush of outward air may be sufficiently strong to cause the ventilator tubing to become dislodged from the tracheostomy tube.

In pediatric patients and infants, the mere weight of the tubing may be sufficient to cause it to become dislodged from the smaller more delicate tracheostomy tube required for infant assisted breathing. Also many times, a pediatric patient, because of loneliness will pull the tubing away from the tracheostomy tube to sound an alarm so that medical staff will come to the patient to provide desired but unnecessary attention.

Finally, particularly when dealing with infants and pediatric patients, the soft tender neck skin of the patient will breakdown, due to the skin of the patient making continual intimate contact with the hard plastic surface of the tracheostomy tube, and because of bodily fluid secretions at about the tracheostomy tube. Moreover, because infants have short necks, the under chin neck skin many times may become pinched between the interconnecting ventilator tube coupler and the tracheostomy tube housing.

Therefore it would be highly desirable to have a new and improved skin protection device that helps to facilitate maintaining a constant fluid and mechanical interconnection between the ventilator tube coupler and the tracheostomy tube while simultaneously helping to substantially prevent skin breakdown.

One attempt at solving the above-mentioned interconnection problem has been to utilize rubber bands to secure the tracheostomy tube to the ventilator tube coupler. While this method may help to retain the tracheostomy tube and the ventilator tube coupler in mechanical interconnection, such rubber bands easily break and snap against the tender skin of the patient. Such unwanted breakage causes undesired trauma that often distracts the attending medical staff from carrying out their normal responsibilities.

Another proposed solution has been to tie a string between the tracheostomy tube and the ventilator tube coupler to hold them together. This method has not proven to be entirely satisfactory, as many times the tracheostomy tube and ventilator tube coupler must be quickly detached from one another to facilitate the removal of bodily fluids from the airway passage of the patient. Moreover, the utilization of strings or rubber bands does not solve the problems associated with skin breakdown or pinching.

Therefore it would be highly desirable to have a new and improved skin protection device that helps protect the skin of the patient from becoming pinched between the interconnecting tracheostomy tube and ventilator tube coupler.

SUMMARY OF THE INVENTION

According to one preferred embodiment of the present invention, there is provided a skin protection device that helps maintain the fluid and mechanical interconnection between a surgically implanted tracheostomy tube and an associated ventilator tube coupler while simultaneously substantially spacing the hard plastic surfaces of the tracheostomy tube external housing from the soft tender neck skin of a patient user. The skin protection device generally includes a fabric covered U-shaped elastic cradle member that is removably attached to the tracheostomy tube external housing to space the housing from the skin of the patient. The cradle member once attached to the tracheostomy tube housing is pulled into tension and sufficiently extended in length to pass over an end portion of the ventilator tube coupler where it is released to engage in tension the ventilator tube coupler and the external housing of the tracheostomy tube to help retain or maintain their fluid and mechanical interconnection.

In accordance with another preferred embodiment of the present invention, the skin protection device includes a securing arrangement that is integrally connected to the cradle member so that it may be removably secured to the ventilator tube coupler to further maintain the mechanical and fluid interconnection between the tracheostomy tube and the ventilator tube.

In accordance with still yet another preferred embodiment of the present invention the skin protection device is provided with a removably attachable cradle cover. The cradle cover is provided for attachment to the cradle member between its spaced apart tracheostomy attachment arms to cover the mechanical interconnection between the tracheostomy tube housing and the ventilator tube coupler to help prevent the soft under chin neck skin of the patient from becoming pinched in the interconnection when the tracheostomy tube and the ventilator tube coupler are mechanically interconnected with one another.

In still yet another preferred embodiment of the present invention, the skin protection device includes a cradle member having a generally horseshoe or ring shape configuration to wrap the cradle around the tracheostomy tube housing to space it from the skin of the patient. An attachment arrangement at the open ends of the cradle member permit the open ends of the cradle to be secured together to help retain the skin protection device to the tracheostomy tube housing.

BRIEF DESCRIPTION OF THE DRAWINGS

The above mentioned features of embodiments of the present invention and the manner of attaining them will become apparent, and the invention itself will be best understood by reference to the description of the best mode and accompanying drawings wherein.

BEST MODE FOR CARRYING OUT THE INVENTION

Figure 1:
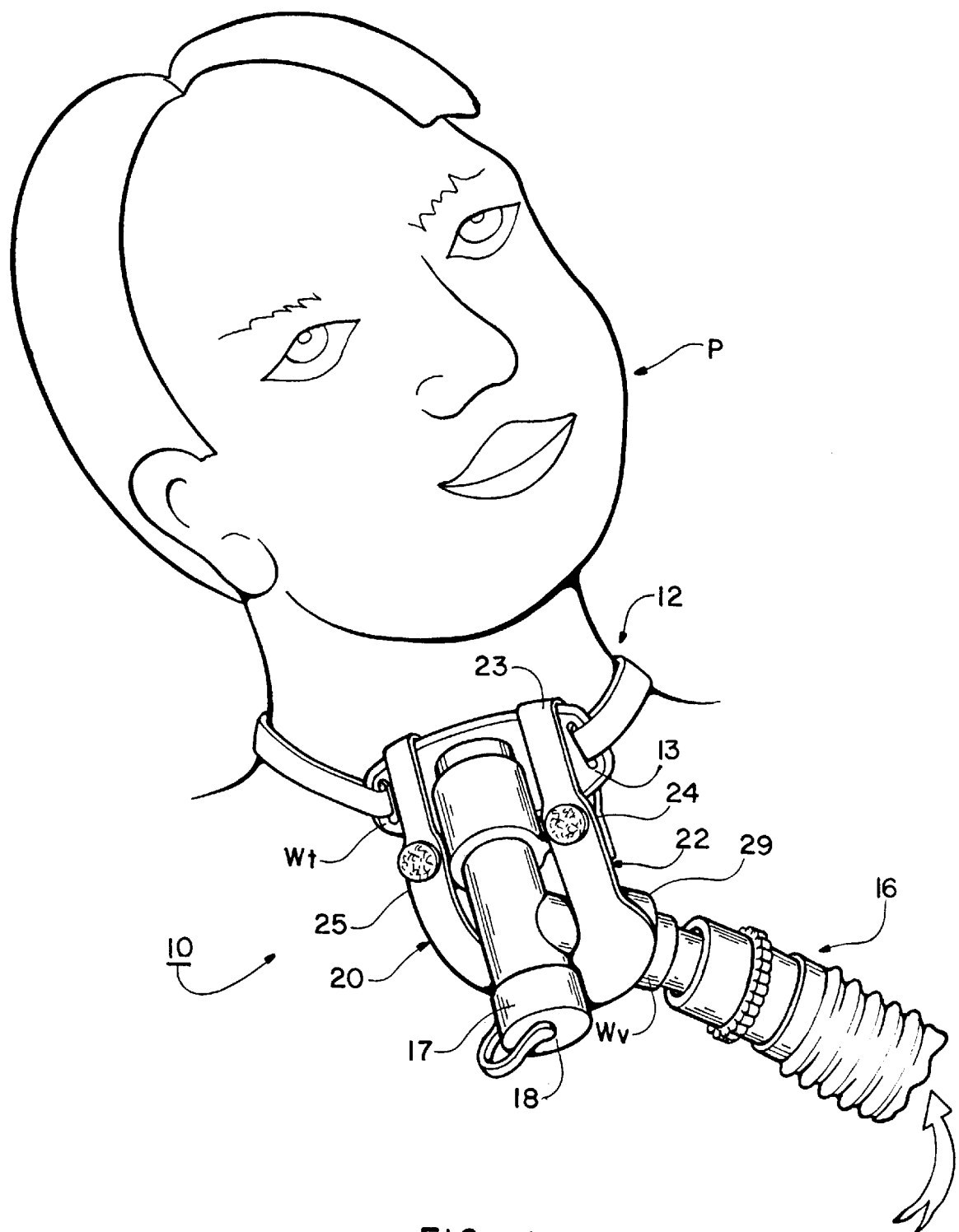
FIG. 1 is a pictorial view of a skin protection device that is constructed in accordance with the present invention, illustrating the device attached between a tracheostomy tube and ventilator tube.

Referring now to the drawings, and more particularly to FIGS. 1–4 thereof, there is shown a skin protection device 10, that is constructed in accordance with a preferred embodiment of the present invention. The protection device 10 as will be explained hereinafter in greater detail, helps to retain or maintain a fluid interconnection between an tracheostomy tube 12 and a ventilator tube 16 while simultaneously protecting the soft tender neck skin of a patient P from becoming irritated due to intimate contact with the hard plastic skin engaging surfaces of the tracheostomy tube 12. Moreover, the protection device 10 also helps protect the soft tender under chin neck skin of premature newborn infants from becoming pinched between the tracheostomy tube 12 and the ventilator tube 16 when they are joined mechanically together for patient assisted breathing. Considering now the protection device 10 in greater detail with reference to FIGS. 1–4, the protection device 10 generally comprises an irregularly shaped cradle member 20 having a unitary construction. The cradle member 20 performs two primary functions. First the cradle member 20 helps to retain the mechanical interconnection between the proximal external end of the tracheostomy tube 12, hereinafter referred to as a tracheostomy tube housing 13 and the distal end of the ventilator tube 16, hereinafter referred to as a ventilator tube coupler 17, so that the tracheostomy tube 12 and the ventilator tube 16 remain in fluid communication with one another. In this regard, the protection device 10 helps to prevent unwanted and undesired life threating uncoupling of the tracheostomy tube 12 from the ventilator tube 16. Secondly, the cradle member 20 spaces the hard plastic skin engaging surfaces of the tracheostomy tube housing 13 from the soft tender neck skin of the patient P.

In order to space the tracheostomy tube housing 13 from the neck skin of the patient P, the cradle member 20 includes a pair of spaced apart tracheostomy tube attachment arm members or more particularly, an elongated right arm member 22 and an elongated left arm member 25. Each of the respective arm members 22 and 25 are composed of an inert elastic material E that is sufficiently thick to space the tender neck skin of the patient P from the hard plastic exterior skin engaging surfaces of the tube housing 13. In order to further protect the skin of the patient P from the hard plastic surfaces of the housing 13, the outer surface of the arm members 22,25 are covered with a soft moisture repellent fabric F that helps reduce the frictional interaction between the skin of the patient P and the arm members 22 and 25.

Figure 2:
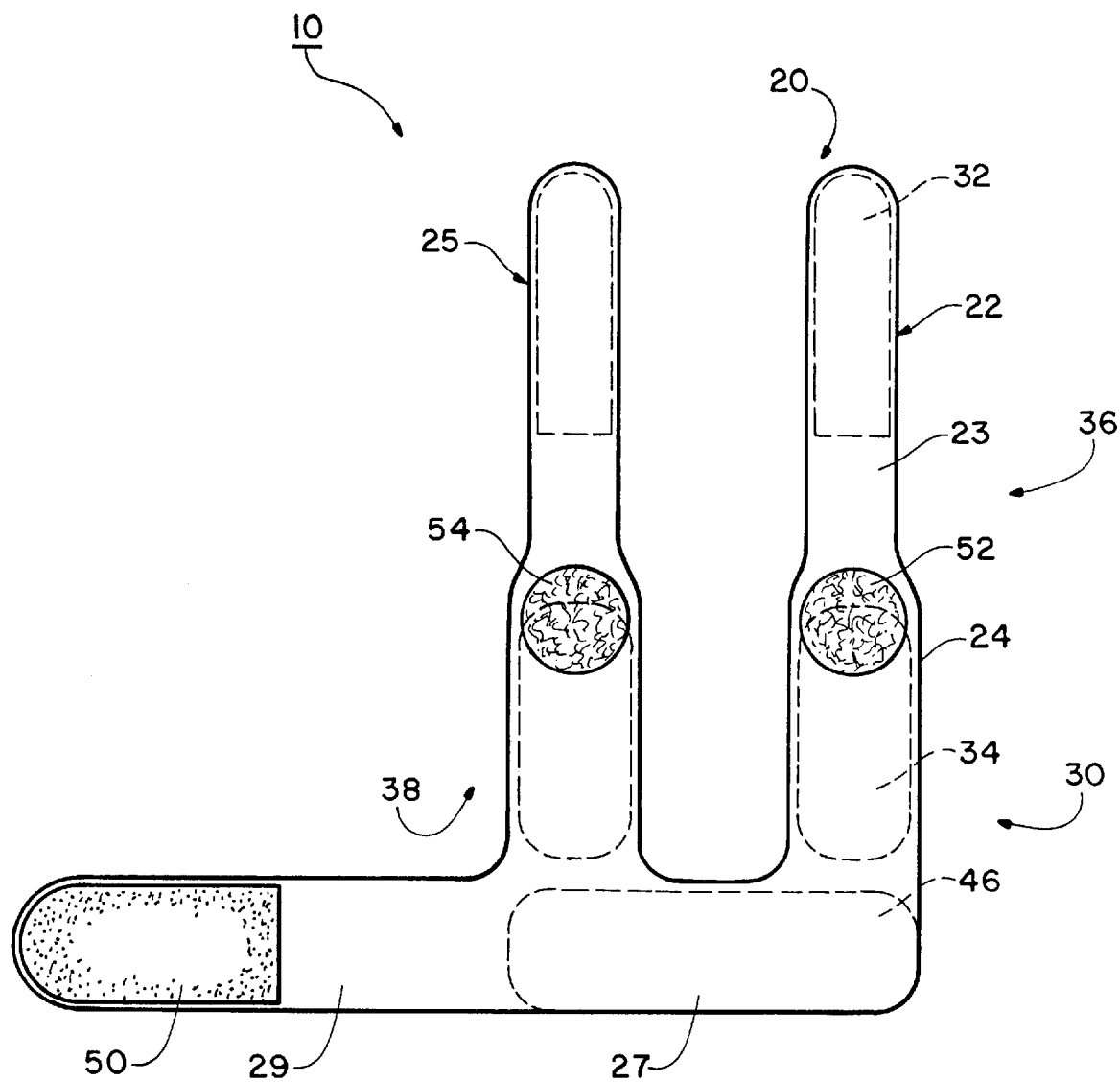
FIG. 2 is a top plane view of the skin protection device of FIG. 1.
Figure 4:
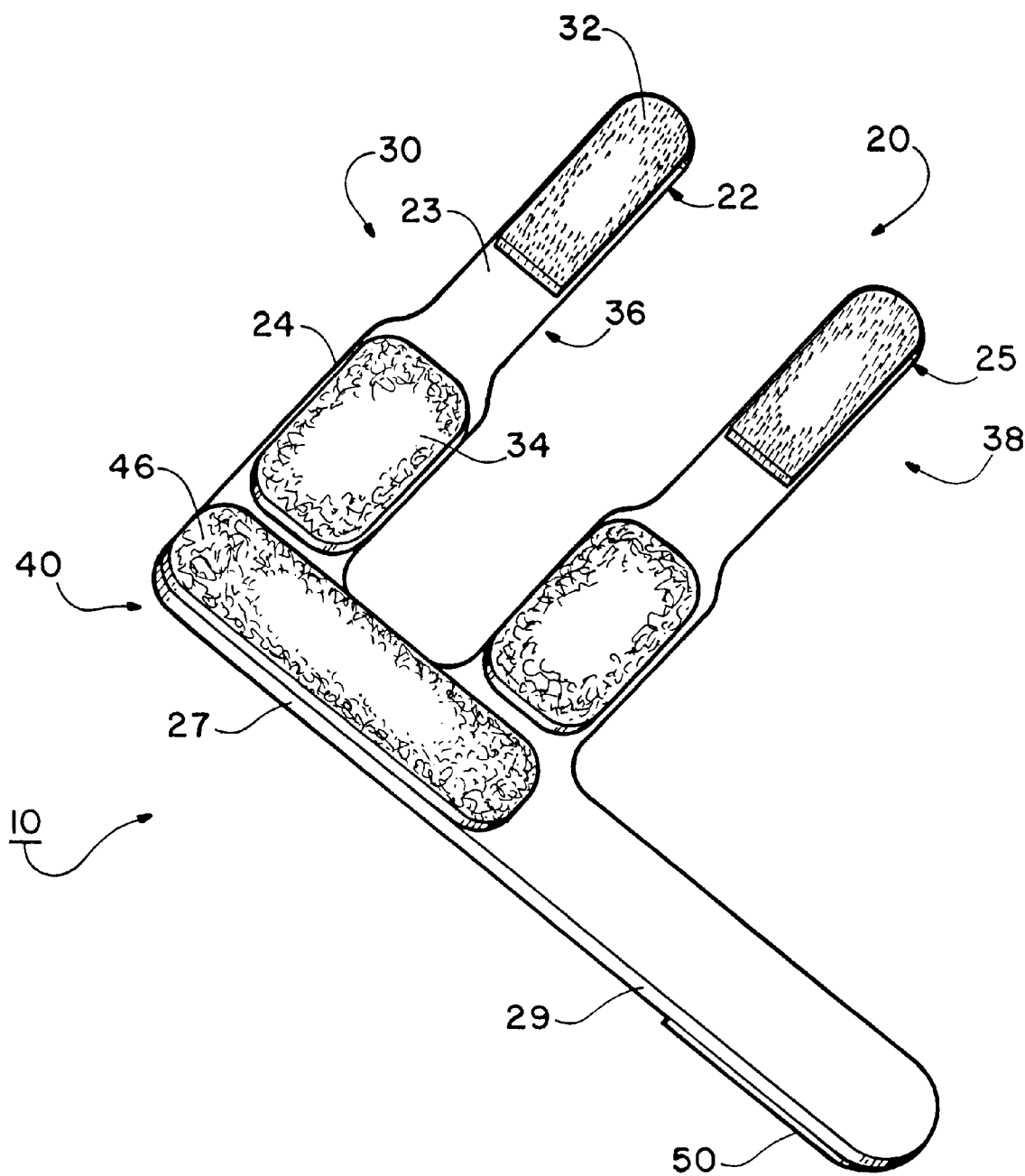
FIG. 4 is a perspective view of the underside of the protection device of FIG. 1.

As best seen in FIGS. 2 and 4, the cradle member 20 also includes a intermediate cross arm member 27 that is integrally connected between the right arm member 22 and the left arm member 25 at their proximal ends to give the cradle member 20 a generally U-shaped structure. The length (L) from the distal end portions of the respective right and left arm members 22, 25 to the cross arm member 27 is selected to be substantially shorter than the distance between the outer surface wall $W_t$ of the tracheostomy tube housing 13 and the outer back wall $W_y$ of the ventilator tube coupler 17 when they are mechanically interconnected with one another. In this regard, when the right arm member 22 and the left arm member 25 are wrapped around and secured to the tracheostomy tube housing 13 and then brought into tension by pulling the cross arm member 27 rearwardly away from the patient P a sufficient distance to enable the cross arm member 27 to engage the outer back wall $W_y$, the tension force of the arm members 22, 25 is coupled between the tracheostomy tube housing 13 and the ventilator tube 16 to help retain them in mechanical and fluid connection.

In order to help secure the protection device 10 to the ventilator tube 16, the cradle member 20 also includes an elongated extension arm 29 that is integrally connected at one end of the cross arm member 27. The extension arm 29 is sufficiently long to loop around the ventilator tube coupler 17 to secure it to the ventilator 16 as will be explained hereinafter in greater detail.

In the preferred embodiment of the present invention, the extension arm 29 is illustrated as extending from the left side of the cross arm member 27. It is contemplated that the extension arm 29 can also be extended from the right side of the cross arm member 27 for securing the protective device 10 to the ventilator tube 16.

To facilitate attaching the protective device 10 to the tracheostomy tube housing 13 and the ventilator tube 16, the protective device 10 includes a right side attachment arrangement indicated generally at 30 and a left side attachment arrangement indicated generally at 38. As the right side attachment arrangement 30 and the left side attachment arrangement 38 are substantially similar in construction, only the right side attachment arrangement 30 will be described hereinafter in greater detail.

Figure 3A:
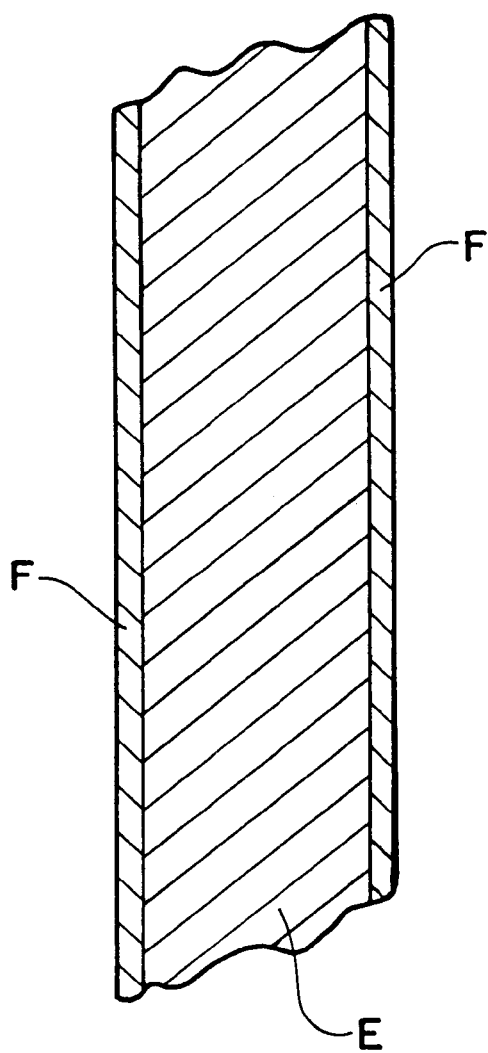
FIG. 3A is a greatly enlarged cross sectional view of the skin protection device of FIG. 3 taken along line A—A.
Figure 3:
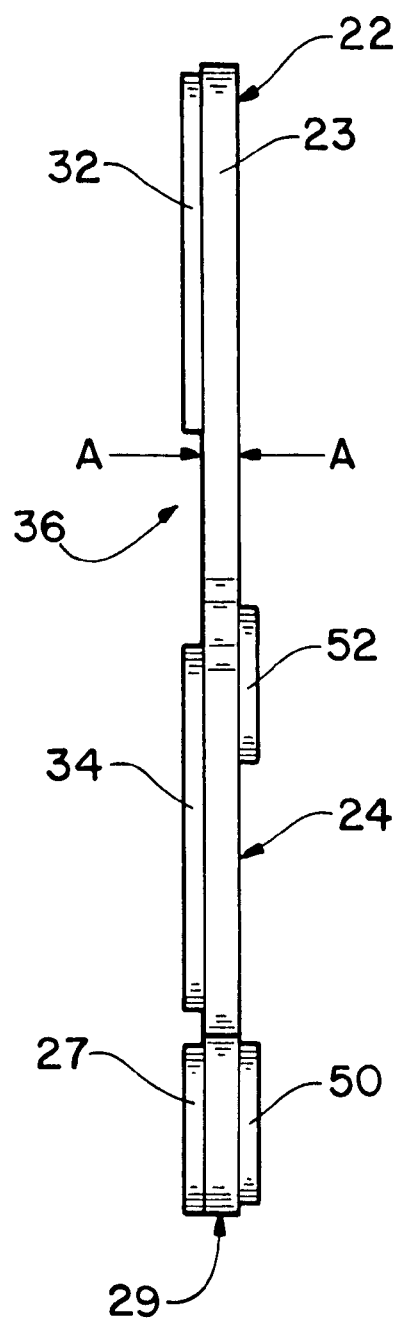
FIG. 3 is a side plane view of the skin protection device of FIG. 1.

Considering now the right side attachment arrangement 30 in greater detail with reference to FIGS. 2–4, the right side attachment arrangement 30 generally includes a pad 32 having a plurality of hooks. The pad 32 is disposed on a narrow distal end portion 23 of the right arm member 22 and is secured thereto by conventional attachment means such as by a waterproof adhesive. Another pad 34 having a plurality of loops or piles is secured on a wide proximal end portion 24 of the right arm member 22.

The pad of hooks 32 and the pad of piles 34 are spaced apart from one another to form a channel 36. The channel 36 is sufficiently wide to permit the narrow distal end portion 23 of the right arm member 22 to unobstructively wrap around the right side of the tracheostomy tube housing 13 without blocking the air passageway of the tracheostomy tube 12 and without the hooks 32 and piles 34 engaging one another. In this regard, once the distal end portion 23 of the right arm member has been looped under and around the right side of the tracheostomy tube housing 13, the distal end portion 23 is pulled into tension to enable the hooks 32 and the piles 34 to securingly removably engage with one another. The securing forces between the hooks 32 and the piles 34 is sufficiently strong to retain engagement as the cross arm member 27 is pulled rearwardly to stretch the wide proximal end portion 24 into tension and to permit the cross arm member 27 to come into engagement with the outer back wall $W_v$ of the ventilator tube 16.

To further facilitate attaching the protective device 10 to the ventilator tube 16, the protective device 10 includes a right side cross arm attachment arrangement indicated generally at 40 and a left side extension arm attachment arrangement indicated generally at 42. The right side cross arm attachment arrangement 40 is disposed on an underside right hand portion 44 of the cross arm member 27 and generally includes a pad 46 of a plurality of piles. The left side extension arm attachment arrangement 42 is disposed on an upper side left hand portion 48 of the extension arm 29 and generally includes a pad 50 of a plurality of hooks. The respective pads of piles 46 and hooks 50 are affixed to respective ones of the cross arm 27 and the extension arm 29 by conventional means, such as by a water proof adhesive.

Figure 5:
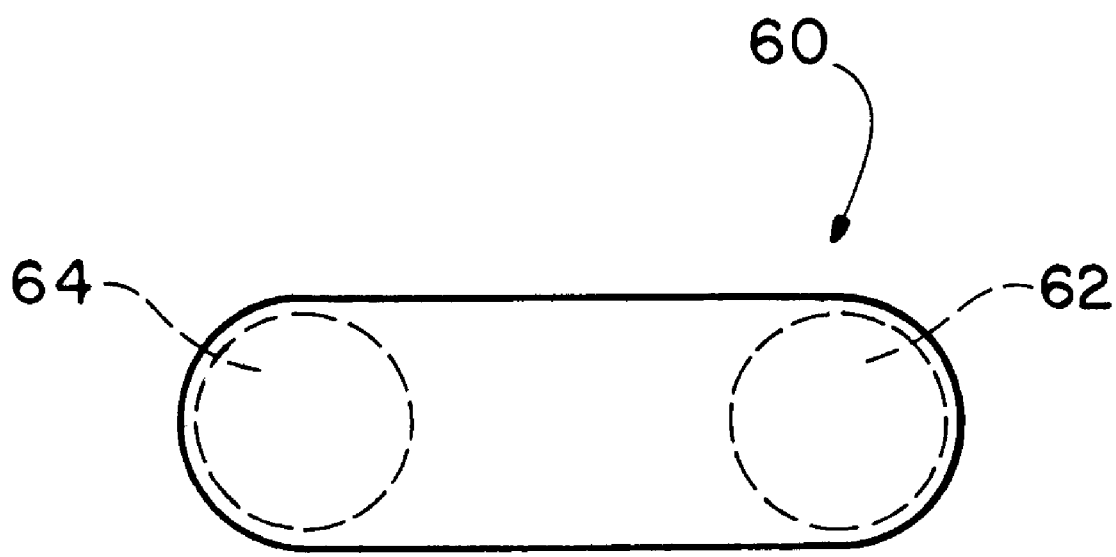
FIG. 5 is a top plane view of another skin protection device that is constructed in accordance with the present invention, illustrating a cradle cover member.
Figure 6:
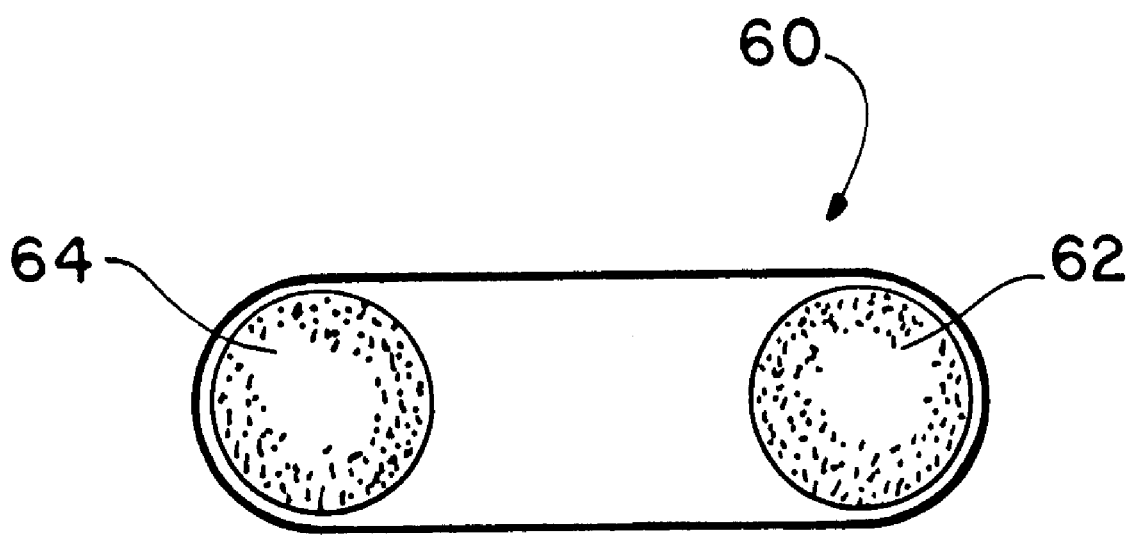
FIG. 6 is a bottom plane view of the cradle cover member of FIG. 5.

In order to protect the soft tender under chin skin of an infant or a short neck person from becoming pinched between the interconnection of tracheostomy tube housing 13 and the ventilator tube coupler 17, the protection device 10 further includes a removably attachable cradle cover 60 as best seen in FIGS. 5 and 6. The cradle cover 60 has a bar like configuration with a pair pads having of a plurality of hooks, such as pads of hooks 62 and 64 that are disposed on opposite ends of the cover 60.

In order to facilitate the removable attachment of the cradle cover 60 to the cradle 20, a corresponding pair of a plurality pads of piles, such as the pile pads 52 and 54 that are disposed on respective ones of the right arm 22 and the left arm 25 at about the connection between their respective proximal end portions, such as for example proximal end portion 24. In this regard, the piles and hooks 52 and 62 removably engage one another while the respective piles and hooks 54 and 64 removably engage one another when the cover 60 is attached between the arms 22 and 25. The cradle cover 60 is disposed on the cradle 20 so as to be above the mechanically interconnection between the tracheostomy tube housing 13 and the ventilator tube coupler 17 to space and cover their interconnection from the under chin skin of the patient P. In this regard, when the tracheostomy tube 12 and the ventilator tube coupler 17 are separated from one another in order to clean fluids from the tracheostomy tube 12, the cover 60 prevents the skin of the patient from becoming pinched between the tracheostomy tube housing 13 the ventilator tube coupler 17 when they are reconnected with one another after such a cleaning process for example.

In use, the protective device 10 is laid on top of the tracheostomy tube housing 13 and the ventilator tube coupler 17 with the cross arm member 27 being disposed furthest away from the tracheostomy tube housing 13. Starting with one of the arm members, for example the right arm member 22, the distal end portion 23 is looped over the housing 13 and brought downwardly and around the housing 13 to space the right side of the housing 13 from the neck skin of the patient P. The distal end portion 23 is then pulled into tension rearwardly a sufficient distance to permit the hooks 32 and the piles 34 to matingly engage with one another. The left arm member 25 is then attached removably to the left side of the housing 13 in a similar manner.

Once the right arm member 22 and the left arm member 25 have been attached to the tracheostomy tube 13, the cross arm member 27 is pulled rearwardly away from the patient P. Pulling the member 27 rearwardly causes the right arm member 22 and the left arm member 25 to stretch into tension. This tension force is a sufficient tension force to help retain or maintain the mechanical coupling between the tracheostomy tube 12 and the ventilator tube 16 when the cross arm member 22 is released into engagement with the outer wall surface $W_v$ of the ventilator tube 16.

In this manner, the tension force exerted by the right arm member 22 and the left arm member 25 is coupled between the respective right and left sides of tracheostomy tube housing 13, and the outer wall of the ventilator tube coupler 17. Such a tension force coupling helps to maintain the fluid coupling between the tracheostomy tube 13 and the ventilator tube 16, while simultaneously protecting the neck skin of the patient P from maintaining intimate contact with the tracheostomy tube housing 14. The soft fabric F of the protection device 10 also helps to protect the skin of the patient P.

To assure the protective device 10 is securely attached to the ventilator tube 16, the extension arm 29 is wrapped around the ventilator tube coupler 17 and stretched into tension a sufficient distance to permit the pad of hooks 50 to matingly engage the pad of piles 46 disposed on the underside of the cross arm member 27. In this manner the protective device 10 is removably secured to the tracheostomy tube 12 and the ventilator tube 16 to facilitate maintaining their mechanical interconnection while simultaneously permitting medical staff to quickly and easily remove the protective device 10 in the event bodily fluids need to be removed from an airway passage of a patient. It should also be understood by those skilled in the art that the hook and pile attachment arrangements so securely mount the protective device 10 to both the tracheostomy tube 12 and the ventilator tube 16 that accidental uncoupling of the tubes 12, and 16 is substantially prevented. Moreover, because of the need to release the cradle tension exerted against the ventilator tube 16, the protective device 10 can not be easily removed by a patient seeking to gain the unnecessary attention of busy medical staff.

Figure 7:
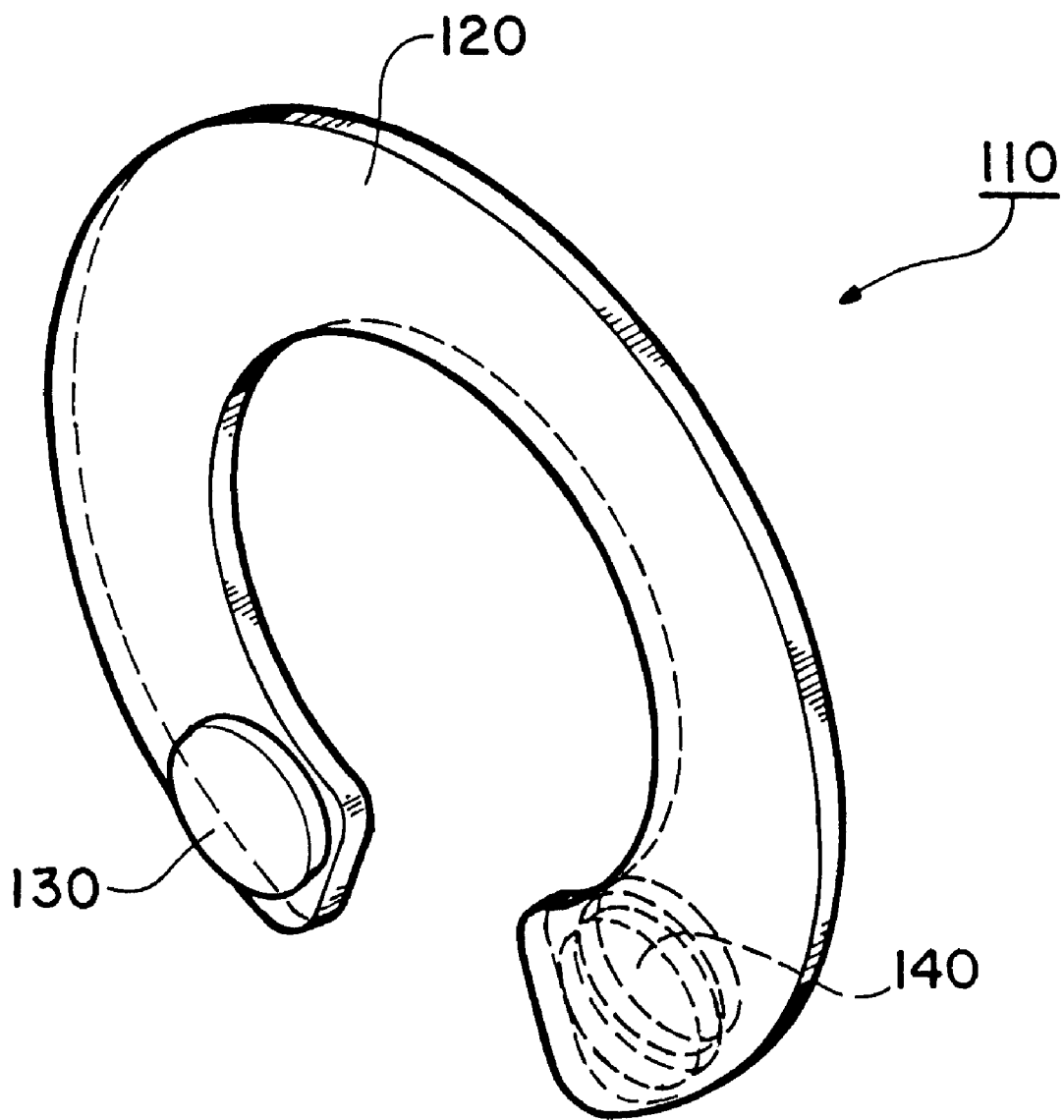
FIG. 7 is a perspective view of another skin protection device that is constructed in accordance with the present invention.
Figure 8:
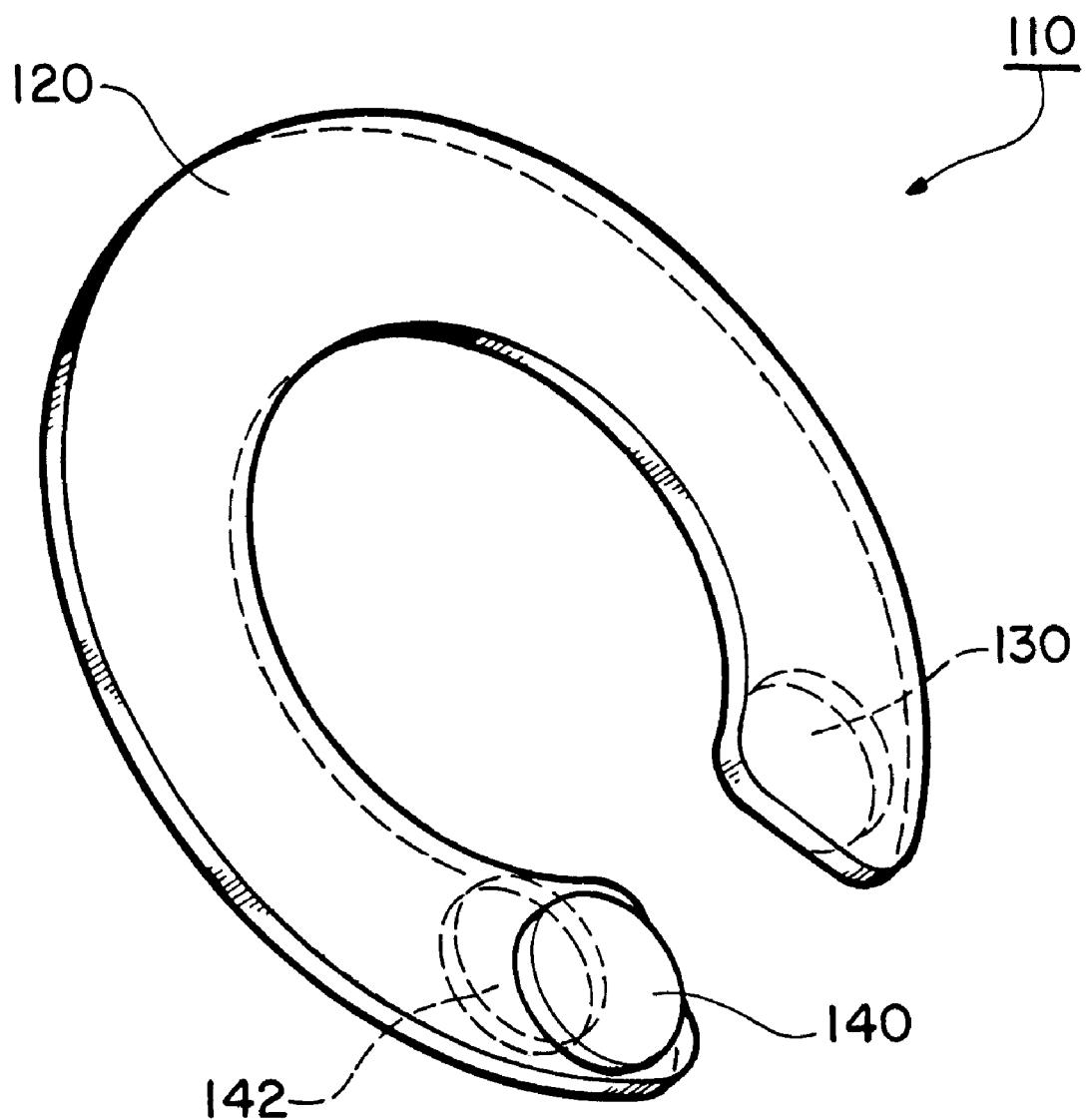
FIG. 8 is another perspective view of the skin protection device of FIG. 7 illustrating its reverse side.

Referring now to the drawings and more particularly to FIGS. 7–8, there is shown another skin protection device 10 that is constructed in accordance with the present invention. The skin protection device 110 includes a cradle member 120 that has a generally ring or horseshoe shape and is constructed of a an inert elastic material E that is sufficiently thick to space the tender neck skin of the patient P from the hard plastic exterior skin engaging surfaces of the tracheostomy tube housing 13.

In order to further protect the skin of the patient P from the hard plastic surfaces of the housing 13, the outer surface of the cradle member 120 is covered with a soft moisture absorbent fabric F that helps protect the skin of the patient P from excreted bodily fluids. The fabric F also helps reduce the frictional interaction between the skin of the patient P and the cradle member 120.

In order to permit the cradle member 120 to be attached to the tracheostomy tube housing 13, the protection device 110 also include an attachment arrangement indicated generally at 130. The attachment arrangement 130 includes a pad 132 of a plurality of hooks disposed at one of the distal ends of the cradle 120 and another pad 140 of a plurality of piles disposed at the other distal end of the cradle 120 but disposed on an opposite side thereof In use, the distal ends of the cradle 120 are stretched to wrap around the tracheostomy tube housing 13 so the respective pads 130 and 140 can be brought into removable engagement with one another.

From the foregoing, it should be understood by those skilled in the art that when the patient P is able to breath periodically without assistance from the ventilator, the device 110 can be used without attachment to the ventilator tube 16. Thus, the device 110 protects the skin of the patient P from breakdown in a manner similar to the device 10.

While particular embodiments of the present invention have been disclosed, it is to be understood that various different modifications are possible and are contemplated within the true spirit and scope of the appended claims. For example, the arrangement of piles and hooks could be easily reversed to accomplish the same results. Likewise, rather than utilizing a waterproof adhesive to affix the pads of hooks and piles to the device 10, other forms of attachment can be employed such as by sewing the pads to the device 10. Therefore there is no intention of limitations to the exact abstract or disclosure herein presented.

We claim:

1. A skin protector, comprising:

a flexible elongated right arm member for wrapping about a right side portion of a tracheostomy tube housing for helping to space the right side portion of the housing from the neck skin of a patient;

a right side attachment arrangement fixed to said right arm member for helping to removably secure said right arm member to the right side portion of said tracheostomy tube housing;

a flexible elongated left arm member for wrapping about a left side portion of said tracheostomy tube housing for helping to space the left side portion of the housing from the neck skin of the patient;

a left side attachment arrangement fixed to said left arm member for helping to removably secure said left arm member to the left side portion of said tracheostomy tube housing; and an cross arm member integrally connected between a distal end of the right arm member and a distal end of the left arm member for cooperating with said right arm member and said left arm member to help maintain an established fluid interconnection between said tracheostomy tube housing and a ventilator tube coupler;

said cross arm member for coupling a tension force against a back wall portion of the ventilator tube coupler to hold it in fluid and mechanical engagement with said tracheostomy tube housing; and said tension force being established when the distal end portions of said left arm member and said left arm member are sufficiently stretched in tension to enable said cross arm member to pass over said ventilator tube coupler and be released in tension against said back wall portion of the ventilator tube coupler.

2. A skin protector according to claim 1, wherein said right arm member and said left arm member each include a soft fabric outer covens for helping to reduce frictional interaction between the skin of the patient and respective ones of the right arm member and the left arm member.

3. A skin protector according to claim 1, wherein said right arm member, said left arm member and said cross arm member are each composed of an inert elastic material that is sufficiently thick to space the skin of the patient from the surface of said tracheostomy tube housing.

4. A skin protector according to claim 3, further comprising:

a cross arm attachment arrangement fixed to said cross arm for helping to facilitate the attachment of a distal end portion of said extension arm member to the one end of said cross arm member; and an extension arm attachment arrangement fixed at about said distal end portion of said extension arm member for engaging said cross arm attachment arrangement for further helping to facilitate the attachment of the distal end portion of said extension arm to the one end of said cross arm member so the extension arm member is secured removably to the ventilator tube coupler to help maintain the established fluid interconnection between said tracheostomy tube and the ventilator tube coupler.

5. A skin protector according to claim 1, further comprising:

an extension arm member integrally connected at one end of said cross arm member and having a sufficient length to loop around said ventilator tube coupler to help secure it removably to said tracheostomy tube housing so that a fluid interconnection established between said tracheostomy tube housing and said ventilator tube coupler is helped to be maintained; and wherein said extension arm member further has a sufficient width to overlay the interconnection between said ventilator tube coupler and said tracheostomy tube housing.

6. A skin protector according to claim 1, wherein said right side attachment arrangement and said left side attachment arrangement each include:

a pair of space apart pads, said pads being sufficiently spaced apart from one another to form a sufficiently wide channel to permit the distal end portions of respective ones of the right arm member and the left arm member to unobstructively wrap around the tracheostomy tube housing without blocking the air passageway of the tracheostomy tube housing; and wherein one of said pads is a pad of hooks and wherein the other one of said pads is a pad of piles, said hooks and piles engaging one another when their respective arm members are wrapped around the tracheostomy tube housing to facilitate securing removably their respective arm members to the tracheostomy tube housing.

7. A skin protector according to claim 1, wherein said cross arm member includes a soft fabric outer covering for helping to reduce frictional interaction between the skin of the patient and said another cross arm member.

8. A method of substantially protecting the neck skin of a patient using a tracheostomy tube with a housing and a ventilator with an associated ventilator tube coupler for patient assisted breathing comprising:

providing a skin protector having a flexible elongated right arm member; a right side attachment arrangement fixed to said tight arm member; a flexible elongated left arm member; a left side attachment arrangement fixed to said left arm member; and a cross arm member integrally connected between a distal end of the right arm member and a distal end of the left arm member for cooperating with said right arm member and said left arm member to help maintain an established fluid interconnection between the tracheostomy tube housing and the ventilator tube coupler;

wrapping removably said right arm member about a right side portion of the tracheostomy tube housing to space a right side portion of the tracheostomy tube from the side of the patient;

wrapping removably said left arm member about a left side portion of the tracheostomy tube housing to space the left side portion of the tracheostomy tube from the skin of the patient;

pulling said cross arm member reawardly away from the patient to simultaneously place in tension said right arm member and said left arm member; and releasing said cross arm member against a back wall portion of the ventilator tube coupler to couple a tension force exerted by the rig arm member and the left arm member between the ventilator tube coupler and the tracheostomy tube housing so they maintain fluid and mechanical engagement with one another.

9. A method of substantially protecting the neck skin of a patient according to claim 8, wherein said step of wrapping said right side member includes;

securing removably said right arm member to said right side portion of the tracheostomy tube housing; and wherein said step of wrapping said left side member includes:

securing removably said left arm member to said left side portion of the tracheostomy tube housing.

10. A method of substantially protecting the neck skin of a patient according to claim 9, further comprising:

positioning said cross arm member above a proximal end of the tracheostomy tube housing prior to establishing the fluid and mechanical interconnection between the tracheostomy tube housing and the ventilator tube coupler; and securing said cross arm member between said right arm member and said left arm member to space an area of under chin neck skin of the patient from the mechanical interconnection so the under chin neck skin of the patient is protected from becoming pinched between the ventilator tube and the tracheostomy tube when they are subsequently mechanically joined together.

11. A method of substantially protecting the neck skin of a patient according to claim 10, further comprising:

interconnecting the tracheostomy tube housing and the ventilator tube coupler to establish a mechanical and fluid path between the tracheostomy tube and the ventilator;

pulling said cross arm rearwardly away from the patient to simultaneously place in tension said right arm member and said left arm member; and releasing said cross arm against a back wall portion of the ventilator tube coupler to couple a tension force exerted by the right arm member and the left arm member between the ventilator tube coupler and the tracheostomy tube housing to help them maintain the fluid and mechanical engagement between the tracheostomy tube and the ventilator.

12. A method of substantially protecting the neck skin of a patient according to claim 11, further comprising:

wrapping releasably an extension arm member integrally connected at one end of said cross arm member about the ventilator tube to help facilitate the securing of said extension member base member to the ventilator tube.

13. A method of substantially protecting the skin of a patient according to claim 12 wherein said step of wrapping includes:

securing removably said extension arm member to the ventilator tube coupler to help maintain an established fluid interconnection between sad tracheostomy tube and the ventilator tube.

* * * * *